(12) United States Patent
Gorochow (10) Patent No.: US 11,376,013 B2
(45) Date of Patent: Jul. 5, 2022

(54) IMPLANT DELIVERY SYSTEM WITH BRAID CUP FORMATION

(71) Applicant: DePuy Synthes Products, Inc., Raynham, MA (US)

(72) Inventor: Lacey Gorochow, Raynham, MA (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 54 days.

(21) Appl. No.: 16/686,361

(22) Filed: Nov. 18, 2019

(65) Prior Publication Data

US 2021/0145449 A1 May 20, 2021

(51) Int. Cl.
*A61B 17/12* (2006.01)
*A61B 90/00* (2016.01)
*A61B 17/00* (2006.01)

(52) U.S. Cl.
CPC .. *A61B 17/12172* (2013.01); *A61B 17/12113* (2013.01); *A61B 2017/00323* (2013.01); *A61B 2017/00867* (2013.01); *A61B 2017/12054* (2013.01); *A61B 2090/3966* (2016.02)

(58) Field of Classification Search
CPC ........ A61B 17/17172; A61B 17/12113; A61B 2017/12054; A61B 2017/00323
See application file for complete search history.

(56) References Cited

U.S. PATENT DOCUMENTS

| 3,429,408 A | 2/1969 | Maker et al. |
| 5,108,407 A | 4/1992 | Geremia et al. |
| 5,122,136 A | 6/1992 | Guglielmi et al. |
| 5,250,071 A | 10/1993 | Palermo |
| 5,263,964 A | 11/1993 | Purdy |
| 5,334,210 A | 8/1994 | Gianturco |
| 5,350,397 A | 9/1994 | Palermo et al. |

(Continued)

FOREIGN PATENT DOCUMENTS

| EP | 1985244 A2 | 10/2008 |
| EP | 2498691 | 9/2012 |

(Continued)

OTHER PUBLICATIONS

Extended European Search Report dated Nov. 18, 2020 in European Patent Application No. 20178690.

(Continued)

*Primary Examiner* — Wade Miles
*Assistant Examiner* — Mohammed S Adam
(74) *Attorney, Agent, or Firm* — Troutman Pepper Hamilton Sanders LLP (57) ABSTRACT

An implant system presented herein includes an engagement wire, a pull wire, and a braided implant having a distal ring thereon. The engagement wire has an elongated member with a radially extending engagement feature at its distal end. The braid can be moved from a delivery shape sized to traverse a catheter to an implanted shape sized to occlude an aneurysm neck. When the braid is in the delivery shape, the pull wire and the elongated member extend through the distal ring and the engagement feature is in a distal direction in relation to the distal ring. Once at least a portion of the braid is positioned in the aneurysm, the pull wire and the elongated member can be moved in a proximal direction to engage the engagement feature to the distal ring and move the distal ring proximally, thereby reshaping the braid within the aneurysm.

8 Claims, 9 Drawing Sheets

(56) References Cited

U.S. PATENT DOCUMENTS

| | | |
|---|---|---|
| 5,382,259 A | 1/1995 | Phelps et al. |
| 5,484,409 A | 1/1996 | Atkinson et al. |
| 5,569,221 A | 10/1996 | Houser et al. |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,718 B2 | 3/2018 | Lorenzo |
| 10,285,710 B2 | 5/2019 | Lorenzo et al. |
| 10,292,851 B2 | 5/2019 | Gorochow |
| 10,420,563 B2 | 9/2019 | Hebert et al. |
| 10,517,604 B2 | 12/2019 | Bowman et al. |
| 10,668,258 B1 | 6/2020 | Calhoun et al. |
| 10,806,402 B2 | 10/2020 | Cadieu et al. |
| 10,806,461 B2 | 10/2020 | Lorenzo |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2003/0009208 A1 | 1/2003 | Snyder et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2006/0025801 A1 | 2/2006 | Lulo et al. |
| 2006/0064151 A1 | 3/2006 | Guterman |
| 2006/0100687 A1 | 5/2006 | Fahey et al. |
| 2006/0116711 A1 | 6/2006 | Elliott et al. |
| 2006/0116714 A1 | 6/2006 | Sepetka et al. |
| 2006/0135986 A1 | 6/2006 | Wallace et al. |
| 2006/0206139 A1 | 9/2006 | Tekulve |
| 2006/0247677 A1 | 11/2006 | Cheng et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0055302 A1 | 3/2007 | Henry et al. |
| 2007/0083132 A1 | 4/2007 | Sharrow |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0045997 A1 | 2/2008 | Balgobin et al. |
| 2008/0097462 A1 | 4/2008 | Mitelberg et al. |
| 2008/0281350 A1 | 11/2008 | Sepetka |
| 2008/0300616 A1 | 12/2008 | Que et al. |
| 2008/0306503 A1 | 12/2008 | Que et al. |
| 2009/0062726 A1 | 3/2009 | Ford et al. |
| 2009/0312748 A1 | 12/2009 | Johnson et al. |
| 2010/0114017 A1 | 5/2010 | Lenker et al. |
| 2010/0324649 A1 | 12/2010 | Mattsson |
| 2011/0202085 A1 | 8/2011 | Loganathan et al. |
| 2011/0295303 A1 | 12/2011 | Freudenthal |
| 2012/0035707 A1 | 2/2012 | Mitelberg et al. |
| 2012/0041472 A1 | 2/2012 | Tan et al. |
| 2012/0283768 A1 | 11/2012 | Cox et al. |
| 2013/0066413 A1 | 3/2013 | Jin et al. |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0277084 A1 | 9/2014 | Mirigian et al. |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2015/0005808 A1 | 1/2015 | Chouinard et al. |
| 2015/0025562 A1 | 1/2015 | Dinh et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0022445 A1 | 1/2016 | Ruvalcaba et al. |
| 2016/0157869 A1 | 6/2016 | Elgård et al. |
| 2016/0228125 A1 | 8/2016 | Pederson, Jr. et al. |
| 2016/0310304 A1 | 10/2016 | Mialhe |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |

(56) References Cited

U.S. PATENT DOCUMENTS

| | | |
|---|---|---|
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | von Oepen et al. |
| 2018/0036508 A1 | 2/2018 | Ozasa et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0325706 A1 | 11/2018 | Hebert et al. |
| 2019/0159784 A1 | 5/2019 | Sananes et al. |
| 2019/0192162 A1 | 6/2019 | Lorenzo et al. |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0138448 A1 | 5/2020 | Dasnurkar et al. |
| 2020/0187951 A1 | 6/2020 | Blumenstyk |
| 2021/0001082 A1 | 1/2021 | Lorenzo et al. |

FOREIGN PATENT DOCUMENTS

| | | |
|---|---|---|
| EP | 3092956 A1 | 11/2016 |
| EP | 3501427 A1 | 6/2019 |
| JP | 2006-334408 A | 12/2006 |
| JP | 2012-523943 A | 10/2012 |
| JP | 2013-78584 A | 5/2013 |
| WO | WO 2009/132045 A2 | 10/2009 |
| WO | WO 2012/158152 A1 | 11/2012 |
| WO | WO 2017/066386 A1 | 4/2017 |
| WO | WO 2018/022186 A1 | 2/2018 |

OTHER PUBLICATIONS

Extended European Search Report dated Dec. 18, 2020 in European Patent Application No. 20181340.

Extended European Search Report issued in corresponding European Patent Application No. 20 20 8130 dated Apr. 8, 2021.

Extended European Search Report issued in European Patent Application No. 21 15 6857 dated Jun. 22, 2021.

IMPLANT DELIVERY SYSTEM WITH BRAID CUP FORMATION

FIELD OF INVENTION

The present invention generally relates to medical instruments, and more particularly, to implant system for aneurysm therapy.

BACKGROUND

The invention relates generally to medical devices and more particularly to implant systems and methods for treating vascular defects. For example, the invention can relate to implant systems and methods for treating an aneurysm. Aneurysms are dilations in a blood vessel caused from weakening of a blood vessel wall. The dilation is produced by the pressure exerted by normal blood flow, which can cause the weakened segment of the blood vessel to swell. In some cases, this swelling results in a sac, or balloon-like polyp protruding from the main or parent vessel. Continued growth and/or eventual rupture of the ballooned arterial wall can have devastating results for a patient. As such, unruptured aneurysms should be treated to prevent hemorrhage. Additionally, ruptured aneurysms can be treated to avert a subsequent rupture and/or additional damage.

Some known medical devices and treatment methods used for treating an aneurysm include packing one or more embolic coils into the sac of the aneurysm. In some treatments, a platinum embolic coil is electrolytically separated from a delivery wire, thus inducing a charge in the coil which can cause a thrombotic effect in the aneurysm. However, the use of electricity for separating the coil from the delivery system is not desirable for patients with pacemakers or similar devices. In other treatments, embolic coils are mechanically separated from a delivery tube. Unfortunately, recanalization is a common problem in known procedures, meaning blood flow returns to the aneurysm and can cause the coil-packed aneurysm to swell further. Additionally, such known devices and methods require prolonged procedure times for the patient and correspondingly increased exposure to radiation for the patient. Moreover, such devices and methods do not treat the neck of the aneurysm, which is the area between the stem blood vessel and the sac of the aneurysm.

Another known treatment method includes the use of both embolic coils and a stent. The coils are delivered to the sac of the aneurysm as described above, and the stent is positioned within the parent blood vessel such that a portion of the stent is disposed over the neck of the aneurysm. A stent is often required for treating wide-neck aneurysms to inhibit the embolic coils from protruding into the parent blood vessel. Such procedures have several drawbacks. For one, delivery of two separate types of devices (i.e., coils and a stent) is a more complex procedure, often resulting in a longer procedure time for the patient. The stent may lead to intra-stent stenosis of the blood vessel. Additionally, a patient would likely be required to take a blood thinner indefinitely following the procedure. Moreover, such devices and methods are not suitable for treatment of aneurysms positioned at a bifurcation of the blood vessel (i.e., between adjacent branches of a vessel).

Another known device and treatment method includes the use of a flow diverter delivered to the stem blood vessel adjacent the neck of the aneurysm. Most commonly, the flow diverter is positioned within the parent blood vessel over the neck of the aneurysm to prevent additional blood flow into the aneurysm from the vessel. In current procedures, typically, more than one flow diverter is required per aneurysm to ensure blood flow is appropriately diverted from the aneurysm. Such a device and treatment method has similar drawbacks to the use of a stent, described above. Specifically, the flow diverter may lead to stenosis of the blood vessel and the patient would likely be required to take a blood thinner indefinitely following the procedure. Additionally, many known flow diverters are not suitable for treating an aneurysm positioned at a bifurcation of the blood vessel. Moreover, long term follow-up of patients treated using a flow diverter is showing an increased rate of recanalization to the aneurysm.

Thus, there is a need for improved systems, devices, and methods for treating vascular defects, such as balloon-type aneurysms, as described herein.

SUMMARY

It is an object of the present invention to provide systems, devices, and methods to meet the above-stated needs.

An example implant system can have an engagement wire, a pull wire, and an implant having a distal ring thereon such that the engagement wire and pull wire are configured to engage the distal ring to reshape the implant and disengage the distal ring after the implant is reshaped. The engagement wire can have an elongated member and an engagement feature disposed at a distal end of the elongated member. The implant can have a braid movable from a delivery shape sized to traverse a catheter to an implanted shape sized to occlude an aneurysm neck. The distal ring can be affixed to the braid. When the braid is in the delivery shape, the pull wire and the elongated member can extend through the distal ring and the engagement feature can be in a distal direction in relation to the distal ring. The pull wire and the elongated member can be movable in a proximal direction to thereby engage the engagement feature to the distal ring and move the distal ring proximally. The braid can be movable from the delivery shape to the implanted shape upon a proximal movement of the distal ring.

In some examples, the implant can also include a proximal ring affixed to the braid. When the braid is in the delivery shape, the pull wire and the elongated member can extend through the proximal ring and the proximal ring can be positioned in the proximal direction in relation to the distal ring.

In some examples, the implant system can include a delivery tube detachably attached to the implant. The system can include a loop wire affixed to the delivery tube. The implant can include a detachment feature having an opening therethrough. The loop wire can be extended through the opening in the detachment feature. One or both of the pull wire and the elongated member can extend through the loop wire to inhibit the loop wire from exiting the opening in the detachment feature. In examples wherein the pull wire extends through the loop wire, the pull wire can be movable to exit the loop wire. Additionally, or alternatively, in examples wherein the elongated member extends through the loop wire, the elongated member and the engagement feature can be moveable to exit the loop wire. The loop wire can be movable to exit the opening in the detachment feature when both of the pull wire and the elongated member are free from the loop wire.

In some examples, the delivery tube can include a notch near its distal end. The detachment feature can be positioned within the notch. The detachment feature can be asymmetric about one or more axis.

In some examples, the implant system can include a hollow push rod configured to engage the proximal ring of the implant. The hollow push rod can be used to translate the implant distally, in place of, or in addition to the delivery tube and detachment feature. The hollow push rod can have an inner diameter that is greater than a sum of a diameter of the pull wire and a diameter of the elongated member. The engagement feature can have a diameter that is less than an inner diameter of the distal ring to allow the engagement feature to pass through the distal ring. The inner diameter of the distal ring can be greater than a sum of a diameter of the pull wire and a diameter of the elongated member so that both the pull wire and the elongated member portion of the engagement wire can pass through the distal ring. The inner diameter of the distal ring can be less than the sum of the diameter of the pull wire and the diameter of the engagement feature such that the engagement feature is inhibited from passing through the distal ring when both the pull wire and the elongated member are extended through the distal ring.

An example method for configuring an implant having a distal ring and a tubular braid for delivery can include one or more of the following steps presented in no particular order, and the method can include additional steps not included here. The method can include positioning the distal ring of the implant on a distal end of the tubular braid. Further, an engagement feature can be positioned to extend radially from a distal end of an elongated member. The elongated member can be extended though a lumen of the tubular braid and a lumen of the distal ring. Further, a pull wire can be extended through the lumen of the tubular braid and the lumen of the distal ring such that the pull wire inhibits the engagement feature from passing through the lumen of the distal ring. The method can further include retracting the engagement feature in a proximal direction to secure the implant within an aneurysm. The pull wire can be retracted in a proximal direction from the implant. Further, the engagement feature can be retracted in a proximal direction from the implant such that the implant is disengaged from at least the pull wire and the engagement feature, and disengaging the implant from a delivery tube. The method can further include positioning the implant with the elongated member and the pull wire therethrough within a delivery catheter such that the engagement feature is positioned in a distal direction in relation to the distal ring. A proximal ring can be attached to a proximal end of the tubular braid, and the elongated member and the pull wire can be extended through a lumen of the proximal ring.

In some examples, the method can further include attaching a detachment feature to the proximal ring, detachably attaching the detachment feature to a delivery tube, and positioning the detachment feature in a notch at a distal end of the delivery tube. The method can also further include attaching a loop wire to the delivery tube, extending the loop wire through an opening of the detachment feature, and extending at least the pull wire or an elongated member through an aperture of the loop wire. Additionally, or alternatively, the method can include engaging a distal end of a hollow push rod to the proximal ring such that the hollow push rod is configured to disengage the proximal ring during treatment.

An example method for positioning an implant can include one or more of the following steps presented in no particular order, and the method can include additional steps not included here. The method can include positioning the implant comprising a distal ring thereon within a delivery catheter. Further, a pull wire and an elongated member with an engagement feature thereon can be positioned through a lumen of the distal ring such that the engagement feature is positioned in a distal direction in relation to the distal ring and such that the pull wire inhibits the engagement feature from passing through the lumen of the distal ring. Further, the implant can extend through a neck of an aneurysm. The method can further include reshaping the implant within the aneurysm by retracting the elongated member while the pull wire is extended through the distal ring. This causes the engagement feature to engage the distal ring and move the distal ring proximally. Further, the pull wire can be retracted in a proximal direction from the implant. The method can further include retracting the engagement feature in a proximal direction from the implant such that the implant is disengaged from at least the pull wire and the engagement feature, and disengaging the implant from a delivery tube.

In some examples, the method can further include engaging the delivery tube to the implant, positioning the delivery tube, the implant, the pull wire, and the elongated member within the delivery catheter, and moving the implant distally through the delivery catheter by pushing the delivery tube distally. The method can further include disengaging the delivery tube from the implant by first retracting the pull wire and then the elongated member from an opening in a loop wire attached to the delivery tube thereby allowing the loop wire to disengage the implant. Additionally, or alternatively, the method can further include positioning the delivery tube in a proximal direction in relation to a proximal ring, the proximal ring disposed approximate a proximal end of the implant, wherein the delivery tube is a hollow push rod. Further, the pull wire and the elongated member can be positioned within a lumen of the hollow push rod and within a lumen of the proximal ring. The method can further include, pushing the hollow push rod in a distal direction against the proximal ring, thereby moving the implant distally through the delivery catheter. Further, the proximal ring can be maintained within the delivery catheter while the implant is extended through the neck of the aneurysm and while the implant is reshaped by retracting the elongated member. Further, the elongated member can be retracted while the pull wire is extended through the distal ring. The method can further include engaging the hollow push rod to the proximal ring while the implant is reshaped by retracting the elongated member while the pull wire is extended through the distal ring. Further, the pull wire can be retracted in the proximal direction from the distal ring to remove the pull wire from the lumen of the distal ring. The method can further include retracting the engagement feature in the proximal direction through the distal ring while the pull wire is removed from the distal ring. Further, the pull wire can be retracted in the proximal direction through the proximal ring. The method can further include retracting the engagement feature in the proximal direction through the proximal ring, and retracting the hollow push rod in the proximal direction, thereby disengaging the hollow push rod from the proximal ring.

In some examples, the method can further include securing the implant within the aneurysm.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

In general, example systems described herein can include an implant having an expandable body with a distal ring thereon and a delivery system configured to position and shape the implant in an aneurysm. The implant can be a braid expandable from a deformed configuration in which the implant is shaped to be delivered through a microcatheter to an aneurysm treatment site to a deployed configuration in which the implant is shaped to occlude an aneurysm from within an aneurysm sac. The delivery system can include a pull wire and an engagement wire configured to pass though the lumen of the distal ring and the lumen of the braid. The pull wire and the engagement wire can be retracted in tandem to move the braid to a cup-shaped deployed configuration, thereby providing a mechanical means to adjust the implant within the sac. The engagement wire can have a bead or other such engagement feature at its distal end sized to pass through the collar, and the pull wire can be sized such that when both the pull wire and engagement wire are positioned through the lumen of the distal ring, the engagement feature is inhibited from passing through the distal ring. The system can also be configured such that the pull wire and/or engagement wire functions to mechanically release the implant from the delivery system.

Figure 1:
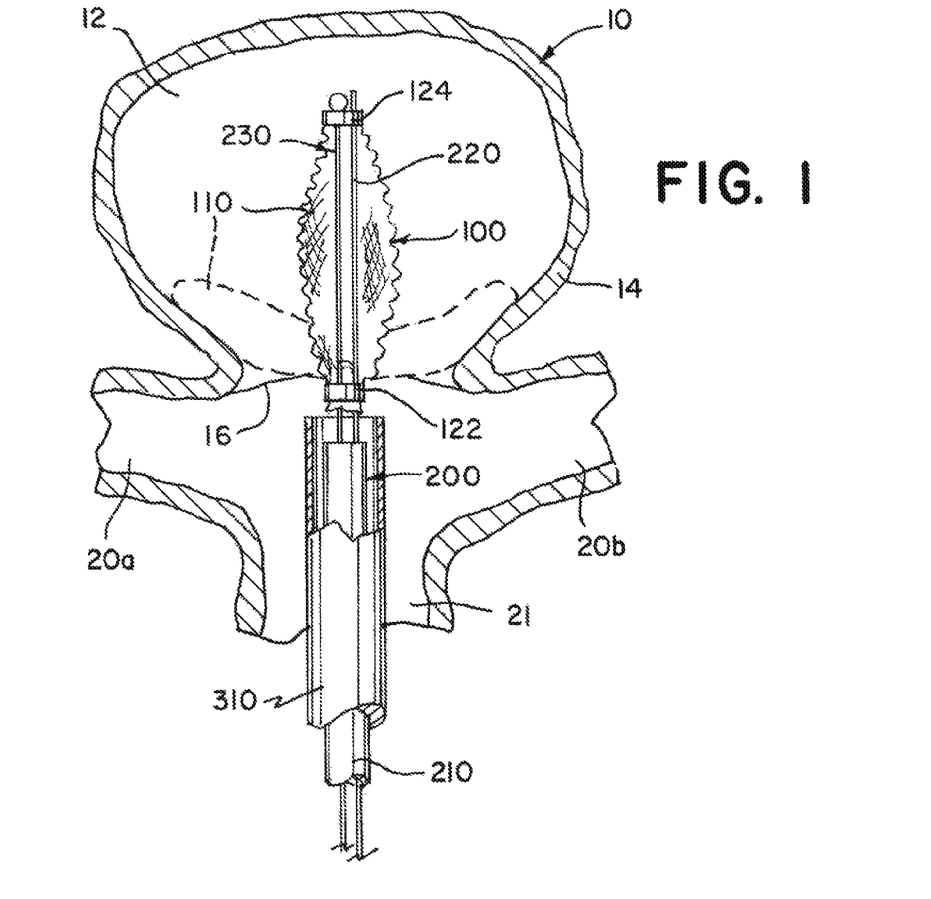
FIG. 1 is an illustration of a system deploying within a cross-section of an aneurysm according to aspects of the present invention.

FIG. 1 depicts a cross-sectional view of an exemplary system. As illustrated, the system can have an implant 100 detachably attached to a delivery system 200. The implant 100 can have a braid 110, a proximal ring 122, and a distal ring 124. Each of the proximal and distal rings 122, 124 can include radiopaque material to aid in positioning of the implant during treatment. Each ring 122, 124 can be welded, glued, or otherwise affixed to the braid 110.

The braid 110 can be constructed from a shape memory alloy, for example, Nitinol or other suitable memory shape material. The braid 110 can have a pre-determined configuration, a deformed configuration, and a deployed configuration. The pre-determined configuration of the braid 110 is the configuration the braid 110 is trained to remember using, for example, via heat treatment. The pre-determined configuration can be a cup-like or a bowl-like shape. The deformed configuration of the braid 110 is the configuration the of the braid 110 while the braid 110 is within the guide catheter 310. In the deformed configuration, the braid 110 can be stretched into an elongated tube-like shape. The braid 110 can be moved from the pre-determined configuration to the deformed configuration so that the braid 110 is sized to traverse the catheter 310 to the aneurysm 10. The deployed configuration of the braid 110 can be based on the pre-determined configuration or a variant of the pre-determined configuration, for example, an asymmetric cup-like configuration. The deployed configuration can be a mutation of the pre-determined configuration, meaning as the braid 110 moves to return to the pre-determined configuration while within an aneurysm 10, it can contact and be constrained by a wall 14 of the aneurysm 10, thereby causing deviations in the pre-determined configuration and yielding the deployed configuration.

The delivery system 200, can have a delivery tube 210, a pull wire 220, and an engagement wire 230. The delivery system 200 can be used to position and deploy the implant 100 within an aneurysm 10. A guide catheter 310 can be used to provide a means to deliver the implant 100 to the aneurysm 10 and/or to assist in the positioning and deployment of the implant 100 within the aneurysm 10.

Figure 2A:
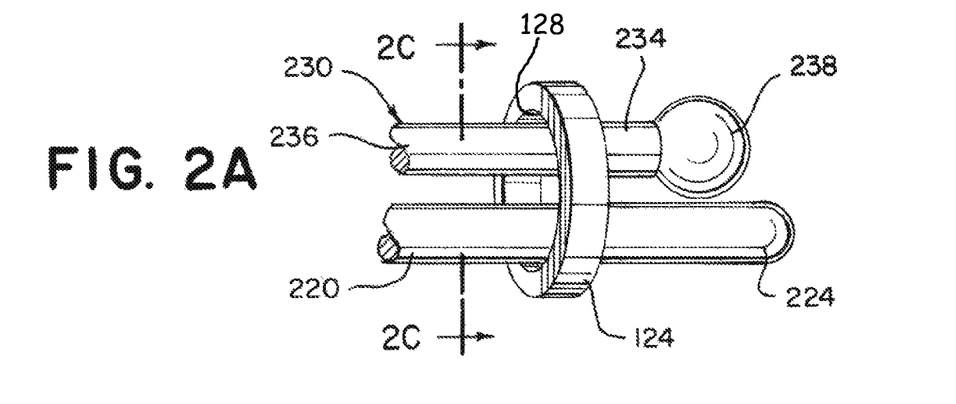
FIGS. 2A to 2C are illustrations of an exemplary distal end of an implant and delivery system according to aspects of the present invention.
Figures 2B, 2C, 3A:
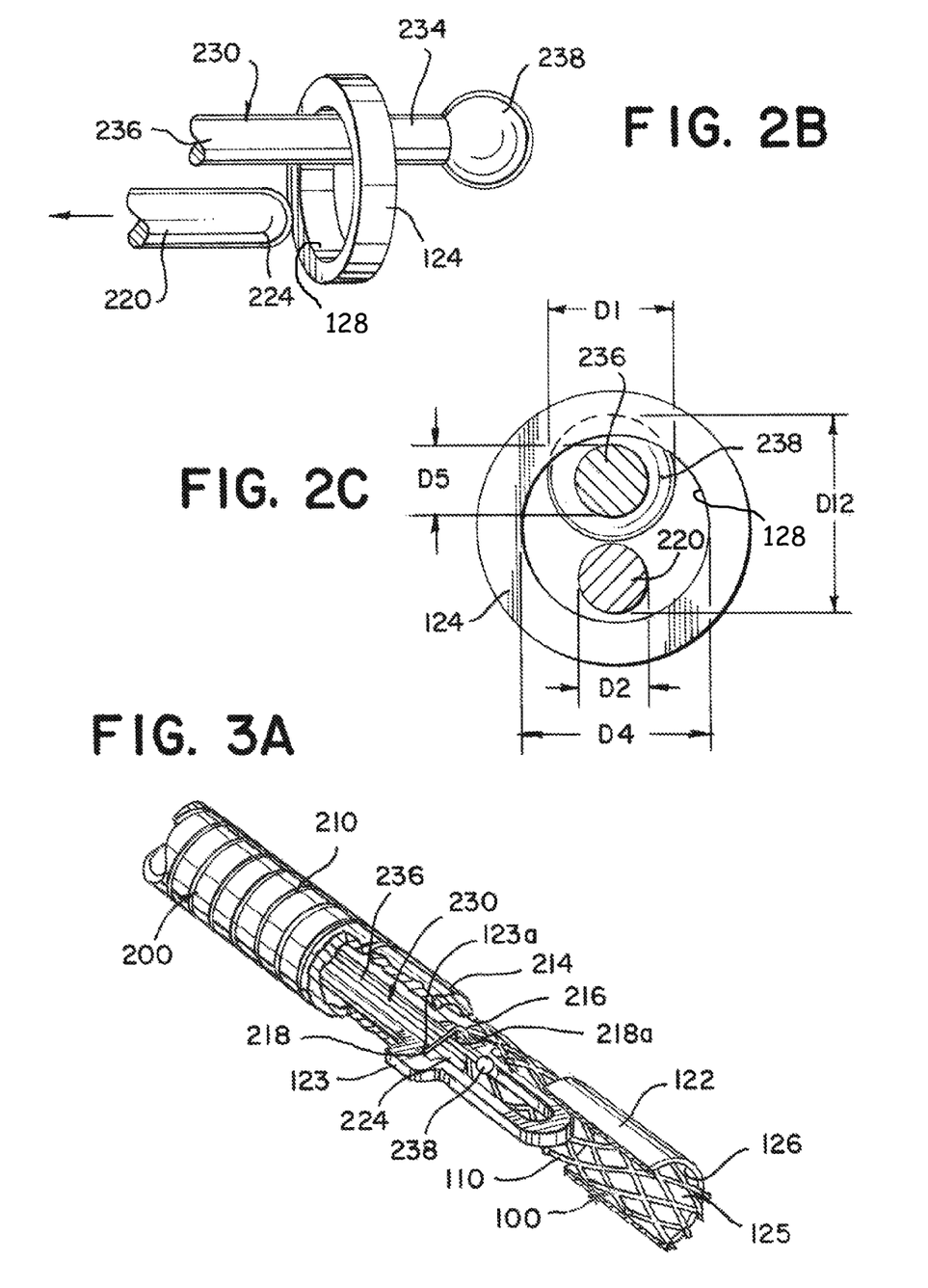
FIGS. 3A and 3B are illustrations of a cut-away views of a delivery system detaching from an implant in an exemplary system according to aspects of the present invention.

FIGS. 2A to 2C are illustrations of a distal end of an exemplary system for assisting the reshaping the implant 100 from the deformed configuration to the deployed configuration. As illustrated, in FIG. 2A, the engagement wire 230 can have an elongated member 236 with an engagement feature 238 attached to the distal end of the elongated member 236. As illustrated, the pull wire 220 and the elongated member 236 are configured to pass through the lumen 128 of the distal ring 124 in a parallel configuration. However, the engagement wire 230 can only pass so far, as the engagement feature 238 cannot pass through the lumen 128 while the pull wire 220 also occupies the lumen 128. Note that the pull wire 220 and engagement wire 230 can either be solid or hollow and made of a material with properties sufficient to permit the interference fit.

FIG. 2B is an illustration of the pull wire 220 retracted from the lumen 128 of the distal ring 124. This position is the beginning of releasing the braid 110, and a proximal force on the engagement wire 230 will release the implant 100. However, even though the interference fit has been released, it can still be reengaged by moving the pull wire 220 back through the lumen 128. This allows the physician to verify placement of the implant 100 in the aneurysm 10 before losing all ability to further move or deform the braid 110.

FIG. 2C is a cross-section view of FIG. 2A. The elongated member 236 can have an elongated member diameter D5. The engagement feature 238 can have an engagement feature diameter D1. The pull wire 220 can have a pull wire diameter D2. A sum of the pull wire diameter D2, and the engagement feature diameter D1 can be a total diameter D12. The distal ring 124 having a ring inner diameter D4. It will be noted that the total diameter D12 is greater than the ring inner diameter D4 resulting in the interference fit, not allowing the engagement feature 238 to retract through the lumen 128 of the distal ring 124 until the pull wire 220 is retracted first. In this configuration, it is clear to see that the engagement feature diameter D1, is less than the ring inner diameter D4, allowing the engagement wire 230 to be retracted from the lumen 128 of the distal ring 124. Different relationships bear out from the above, in that D2+D5<D4 and D1+D2=D12>D4.

Figures 3B, 4:
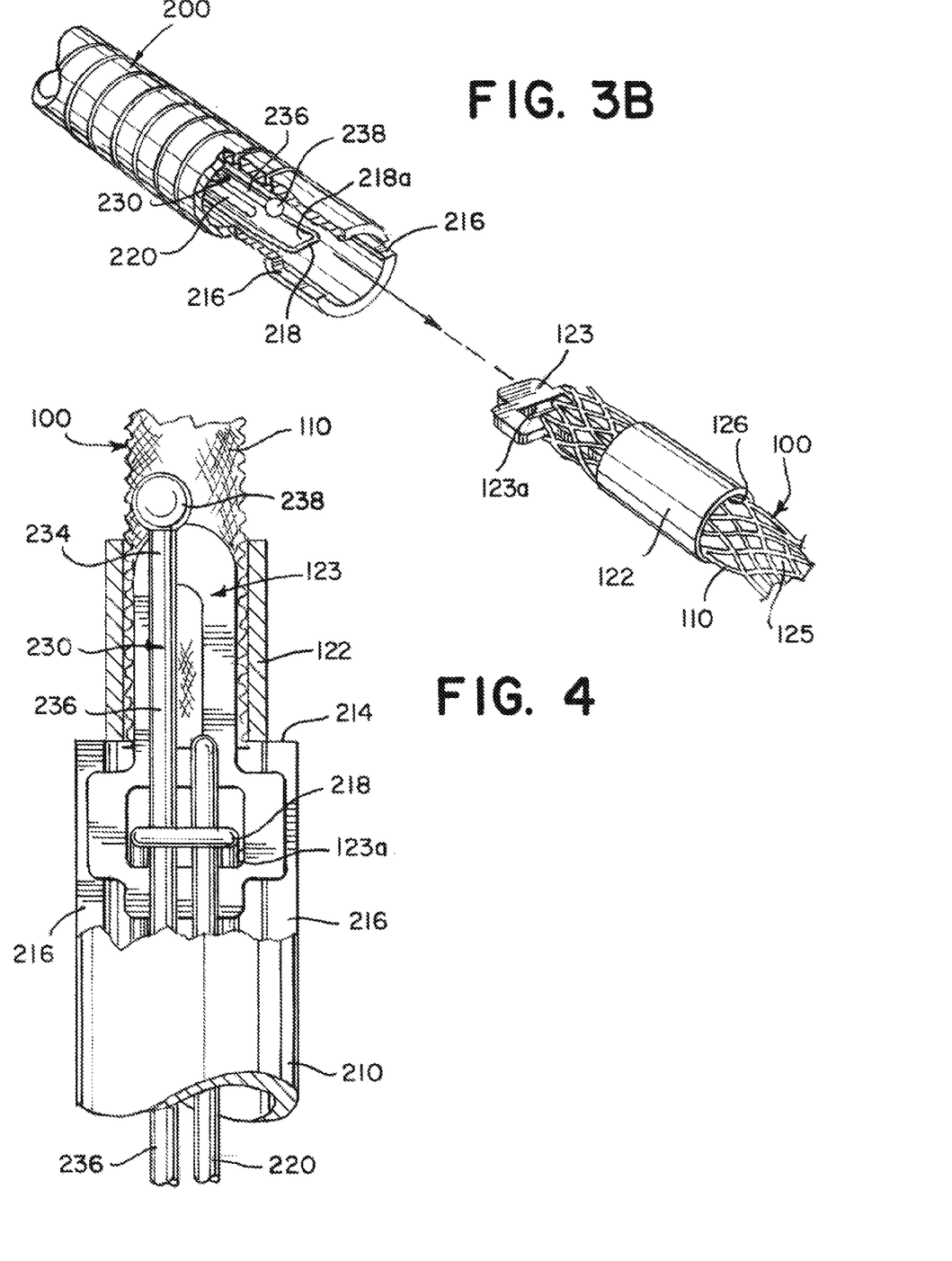
FIG. 4 is an illustration of a cut-away view of an exemplary system according to aspects of the present invention.

FIGS. 3A and 3B are illustrations of a delivery system 200 detaching from an implant 100, where FIG. 3A illustrates the implant 100 detachably attached to the delivery system 200 and FIG. 3B illustrates the implant 100 and delivery system 200 shortly after detachment of the implant 100.

Referring collectively to FIGS. 3A and 3B, the implant can include a detachment feature 123 affixed thereto that is shaped and otherwise configured to detachably engage the delivery system 200. The implant 100 can further include a proximal ring 122. The detachment feature 123 and/or the proximal ring 122 can be constructed of radiopaque material to aid visualization of placement of the implant 100. The proximal ring 122 can serve to constrict the proximal end of the braid 110 and/or the proximal ring 122 can provide a structure to aid in securing the braid 110 to the detachment feature 123.

As illustrated in FIG. 3A, when the implant 100 is attached to the delivery system 200, the pull wire 220 and the engagement wire 230 can be configured parallel to each other and configured to pass through an aperture 218a of a loop wire 218, the lumen 126 of the proximal ring 122 and the lumen 125 of the braid 110. The loop wire 218 can be attached to a delivery tube 210 and can pass through an opening 123a of a detachment feature 123. In this configuration, the loop wire 218 detachably secures the detachment feature 123 to the delivery tube 210. The detachment feature 123 can be attached to the proximal ring 122 of the implant 100 and detachably attached to a notch 216 (See FIG. 4) in the delivery tube 210. The notch 216 can be disposed on a distal end 214 of a delivery tube 210.

The delivery tube 210 can be made of a biocompatible material, such as stainless steel. The tube 210 can be suitably sized for delivering and deploying the implant 100 to an aneurysm 10 as described herein.

As illustrated in FIG. 3B, the pull wire 220 and the engagement wire 230 can be retracted proximally from the aperture 218a of the loop wire 218 and into the delivery tube 210. Upon the pull wire 220 and the engagement wire 230 being retracted into the delivery tube 210, the loop wire 218 falls out of the opening 123a of the detachment feature 123 and no longer secures the detachment feature 123 to the delivery tube 210, thereby enabling the detachment feature 123 to detach from the delivery tube 210.

The loop wire 218 can be relatively small, having the thickness of a hair in some examples, so it can be preferred for the loop wire to be entirely shielded within the delivery tube 210 to prevent damage from accidental contact. The loop wire 218 can be an elongated wire that is bent to form an opening. Alternatively, the loop wire 218 can be a single elongated wire with an opening. The loop wire 218 can be formed from any number of materials, including nitinol and stainless steel.

FIG. 4 is a side cross-sectional view of FIG. 3A. As illustrated, the detachment feature 123 can be seen detachable attached to the notch 216 located at the distal end 214 of the delivery tube 210. Further, the detachment feature 123 can be seen attached to the proximal ring 122. The pull wire 220 and the engagement wire 230 can be seen passing though the aperture 218a of the loop wire 218. The loop wire 218 can be seen passing through an opening 123a of the detachment feature 123 and securing the detachment feature 123 to the notch 216.

Figure 5A:
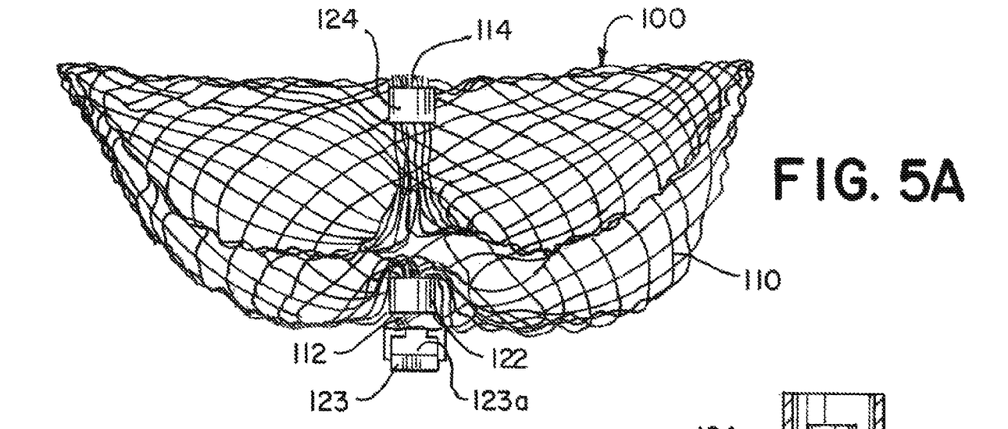
FIGS. 5A to 5C are illustrations of an exemplary implant in a pre-determined state outside the aneurysm, an exemplary implant in a deployed state within a cross-section of the aneurysm, and in a deformed/delivery configuration, respectively, according to aspects of the present invention.
Figures 5B, 5C:
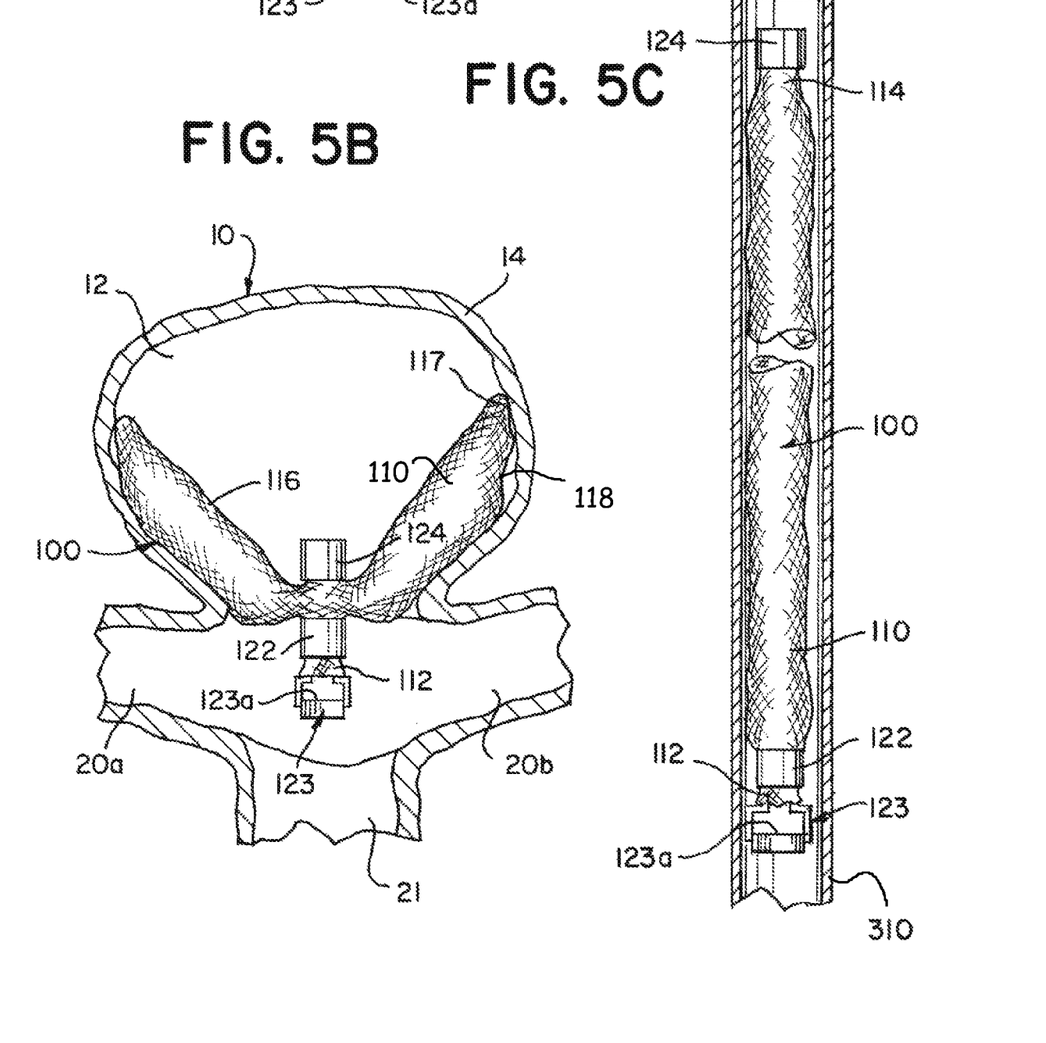

FIGS. 5A to 5C are illustrations of an exemplary implant 100 in the pre-determined configuration outside the aneurysm 10 in the deployed configuration within a cross-section of the aneurysm 10 respectively. The exemplary implant 100 can have a braid 110, a proximal ring 122, a distal ring 124 and a detachment feature 123 such as illustrated and/or described herein or otherwise known by a person of ordinary skill in the art. The proximal ring 122 can be disposed on a proximal end 112 of the braid 110 and the distal ring 124 can be disposed on a distal end 114 of the braid 110. As disclosed above, the detachment feature 123 can have an opening 123a.

As illustrated in FIG. 5A, in the predetermined shape, the braid 110 can have a bowl, or cup shape. The distal and proximal rings 124, 122 can be positioned along a central axis of the braid 110. The braid 110 can be folded such that the bowl defines two nested bowls. The distal and proximal rings 124, 122 can be respectively positioned at the trough of each nested bowl shape.

As illustrated in FIG. 5B, the braid 110 of implant 100, once in the deployed configuration, can have a fold 117, an inner sack 116, an outer sack 118. The fold 117 can be a curvature of the braid 110 that delineates the inner sack 116 from the outer sack 118. The outer sack 118 can contact the wall 14 of the aneurysm 10.

The braid 110 can be include a memory shape material and can be heat-set or otherwise set to form the pre-determined shape. When deformed, the braid 110 can be activated to move to the pre-determined shape due to heat from contact blood or other bodily fluid. Alternatively, the braid 110 need not include memory shape material, and a delivery system 200 such as illustrated and described herein can be sufficient to move the braid 110 from the deformed shape as illustrated in FIG. 5C to the deployed configuration illustrated in FIG. 5B.

As illustrated in FIG. 5C, in the deformed configuration, the implant 100 can be collapsed and/or elongated to fit within a guide catheter 310.

Figure 6A:
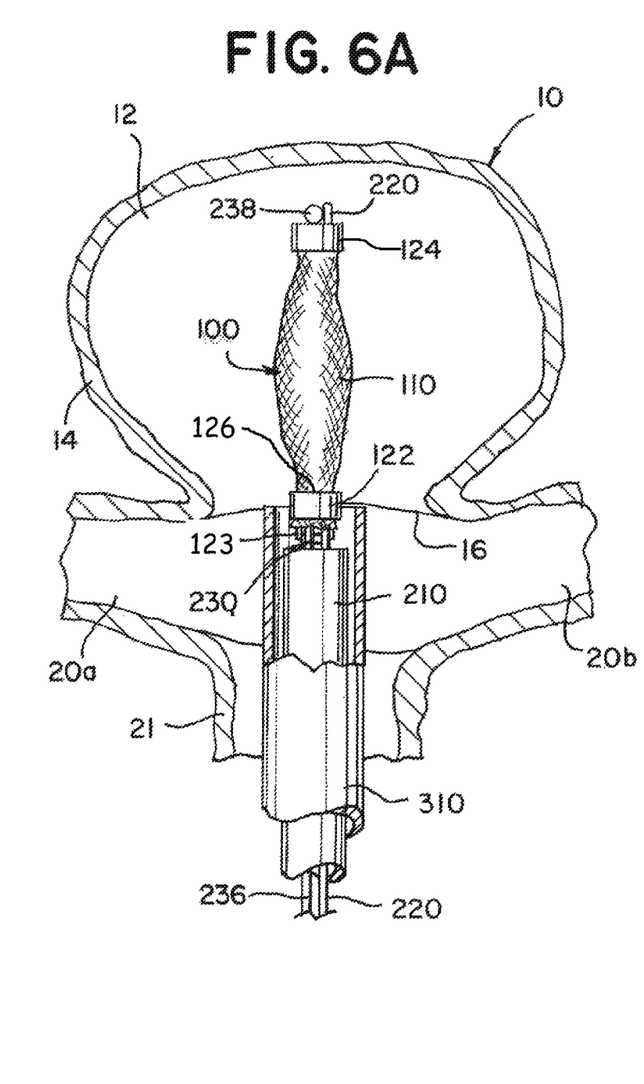
FIGS. 6A to 6D are an illustration of a deployment sequence of an exemplary system according to aspects of the present invention.
Figure 6B:
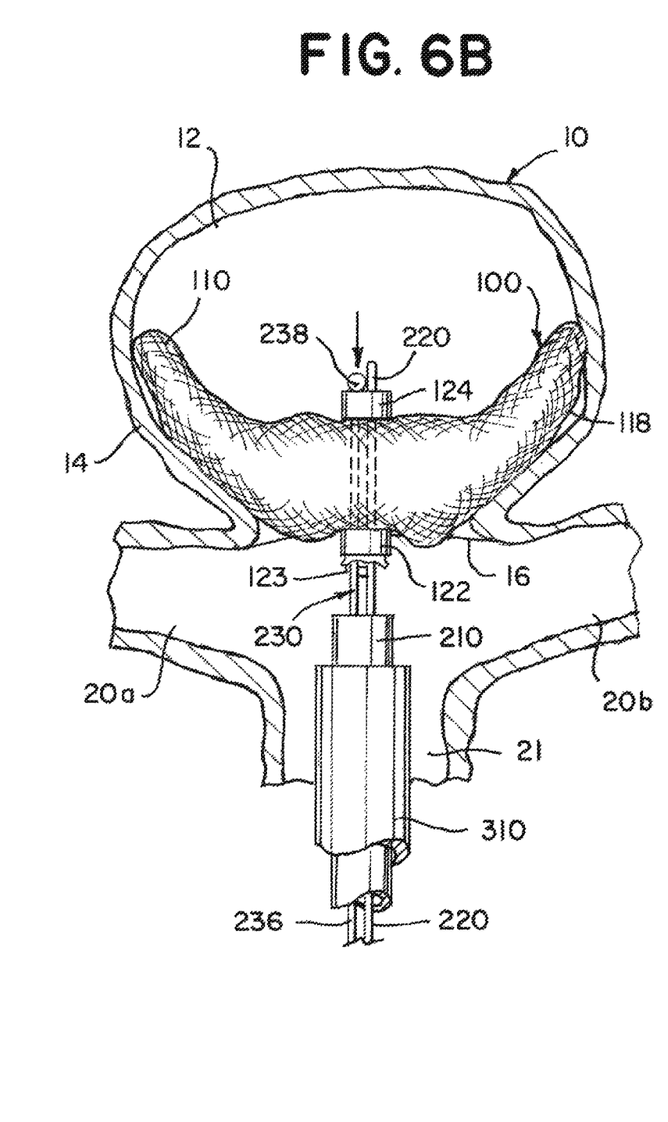

FIGS. 6A to 6D are an illustration of a deployment sequence of an exemplary delivery system 200 and implant 100. As illustrated in FIG. 6A, the implant 100 begins to expand from the deformed configuration within the aneurysm 10 as it exits the catheter 310. In FIG. 6A, the pull wire 220 and the engagement wire 230 are both positioned to pass though the lumen 126 of the proximal ring 122, the lumen 125 of the braid 110 and the lumen 128 of the distal ring 124. The pull wire 220 and the engagement wire 230 can be in the parallel configuration discussed earlier in relation to FIG. 2A or otherwise positioned as described herein. As illustrated in FIG. 6B, the engagement wire 230 and the pull wire 220 can be retracted in a proximal direction such that the distal ring 124 is moved in a proximal direction closer to the proximal ring 122. While the engagement wire 230 and pull wire 220 are being retracted, the braid 110 is reconfigured from the deformed configuration to the deployed configuration such that the outer sack 118 contacts the wall 14 of the aneurysm 10. The implant 100 can include memory shape material, and the implant 100 can reshape based at least in part on the pre-determined shape of the implant 100. Alternatively, in some examples, the braid 110 need not include memory shape material, and in such cases, the movement of the engagement wire 230 and pull wire 220 can be sufficient to reshape the braid 110 to the deployed shape.

Figure 6C:
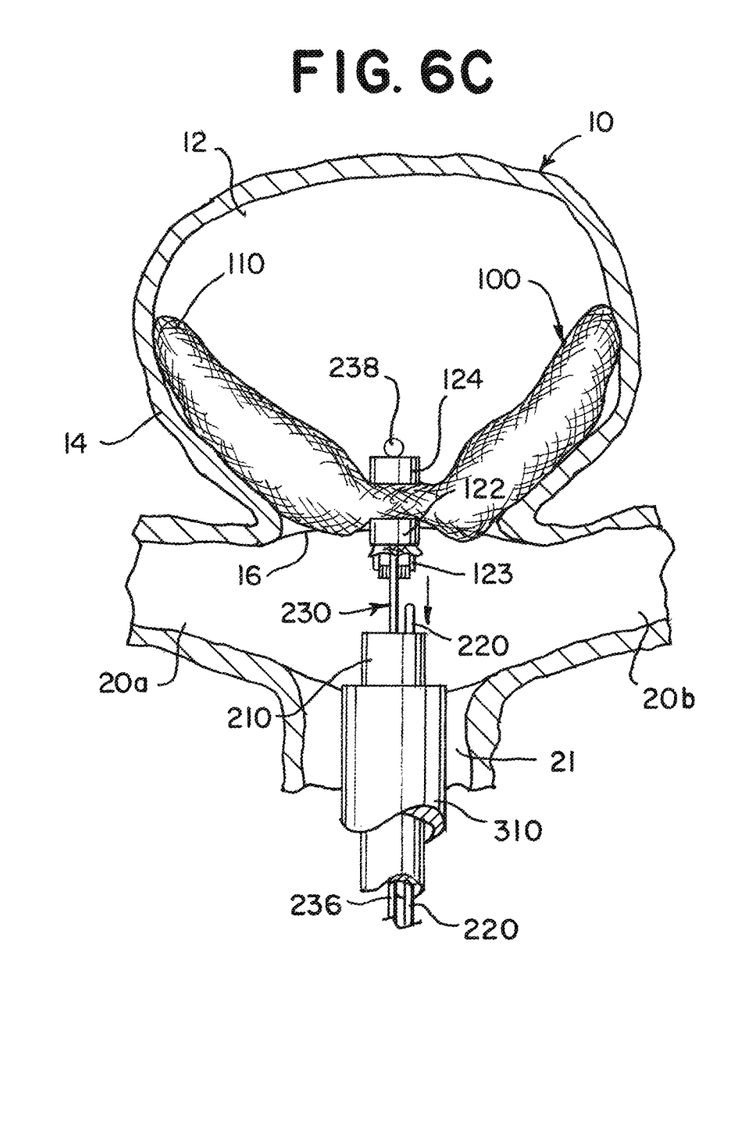

As illustrated in FIG. 6C, the pull wire 220 can be retracted in a proximal direction into the delivery tube 210. A slight adjustment of the engagement wire 230 in the distal direction can be made to allow for the pull wire 220 to be retracted. The pull wire 220 can be configured to pass though the lumen 128 of the distal ring 124, the lumen 125 of the braid 110, the lumen 126 of the proximal ring 122 and the aperture 218a of the loop wire 218. Further details regarding retraction are discussed earlier in FIGS. 2A to 2C.

Figure 6D:
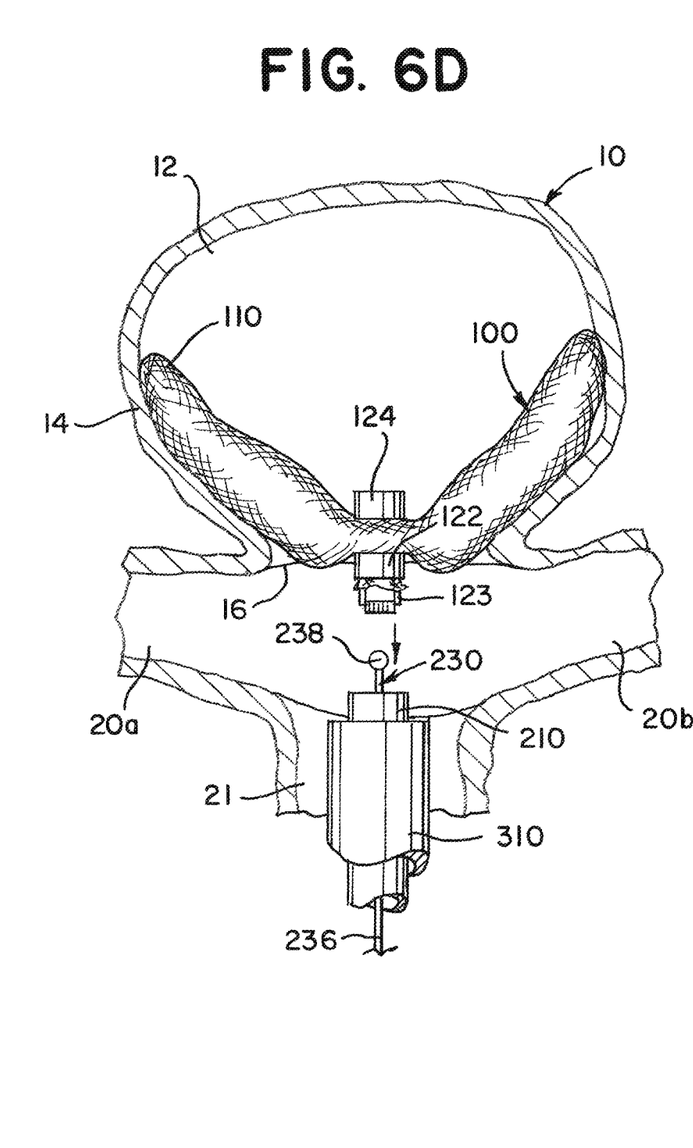

As illustrated in FIG. 6D, the engagement wire 230 can be retracted in a proximal direction into the delivery tube 210. The engagement wire 230 is configured to pass though the lumen 128 of the distal ring 124, the lumen 125 of the braid 110, the lumen 126 of the proximal ring 122 and the aperture 218a of the loop wire 218. Further details regarding retraction are discussed earlier in FIGS. 2A to 2C.

Figures 7A, 7B:
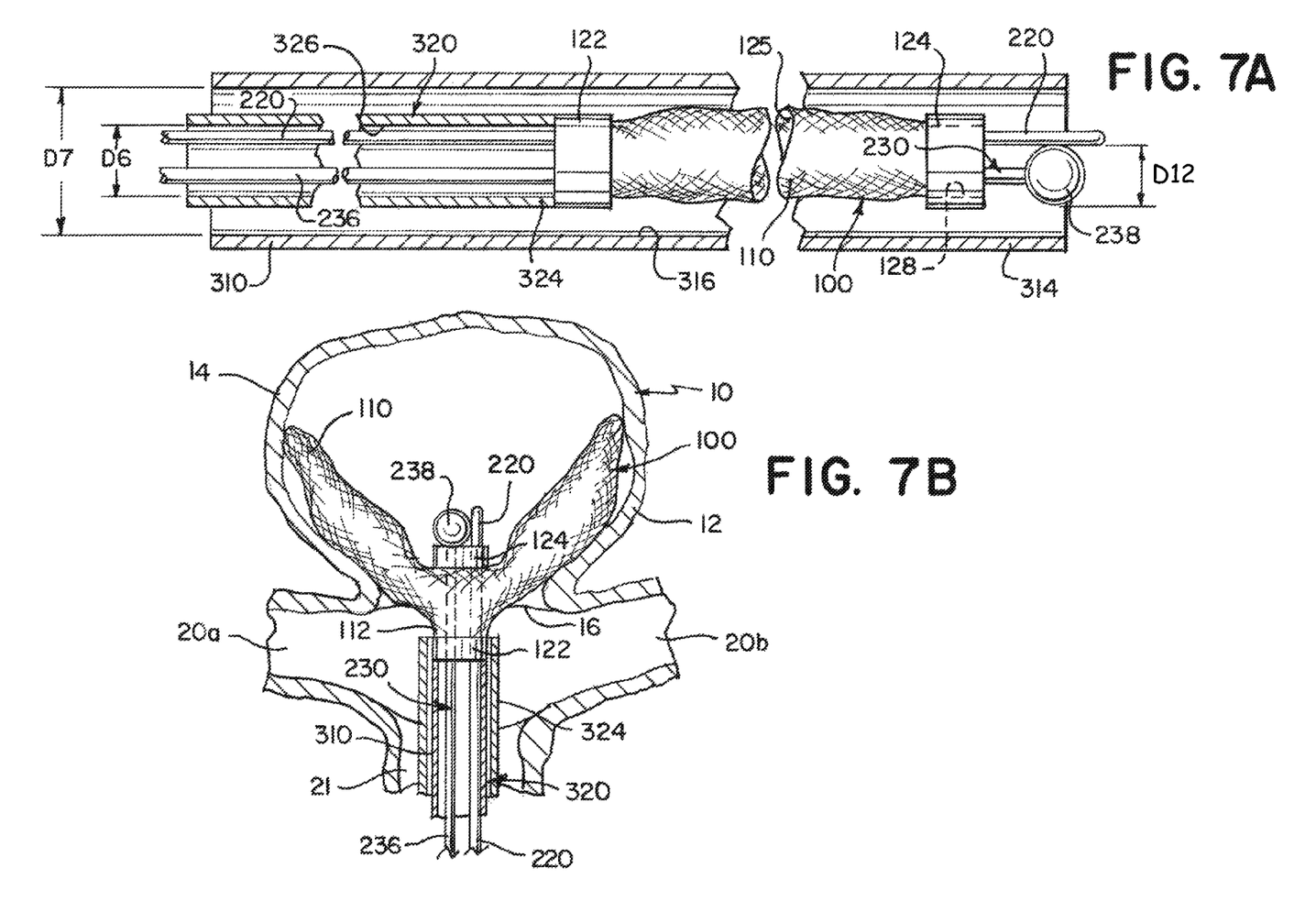
FIGS. 7A and 7B are illustrations of a cross-section of an exemplary system for deploying an exemplary implant into the aneurysm according to aspects of the present invention.

FIGS. 7A and 7B are an illustration of a cross-section of an alternative exemplary delivery system 200 for deploying an exemplary implant 100 into the aneurysm 10.

As illustrated in FIG. 7A, a distal end 324 of a hollow push rod 320, can engage the proximal ring 122 of the implant 100. The lumen 326 of the hollow push rod 320 can be sized to permit the engagement wire 230 and the pull wire 220 to pass though the hollow push rod 320. The hollow push rod 320 can be pushed in a distal direction causing the engaged implant 100 to also be pushed distally towards, and exit out of, a distal end 314 of the guide catheter 310. The implant 100 can be in the deformed configuration, such as illustrated in FIG. 5C. A guide catheter inner diameter D7 can be sized to permit the hollow push rod 320 and the implant 100 to pass though the lumen 316 of the guide catheter 310. A push rod inner diameter D6, is configured such that it is greater than or equal to the total diameter D12.

As illustrated in FIG. 7B, the distal end 324 hollow push rod 320 can remain engaged to the proximal ring 122 as the engagement wire 230 and pull wire 220 are retracted in a proximal direction into the hollow push rod 320. As a result of the reaction, the implant 100 can be moved from the deformed configuration, illustrated in FIG. 7A, to the deployed configuration shown here. The proximal end of the braid 110 can be retained within the guide catheter 310 until after the braid 110 is fully deployed within the aneurysm. After the braid 110 is deployed, the pull wire 220, then the engagement wire 230 can be retracted. Once the pull wire 220 and engagement wire 230 are disengaged from the implant 100, the catheter 310 can be retracted, thereby completing implantation.

Illustrations in the above-described figures depict generally hollow or delivery tubes 210 according to the present invention. When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

Figure 8:
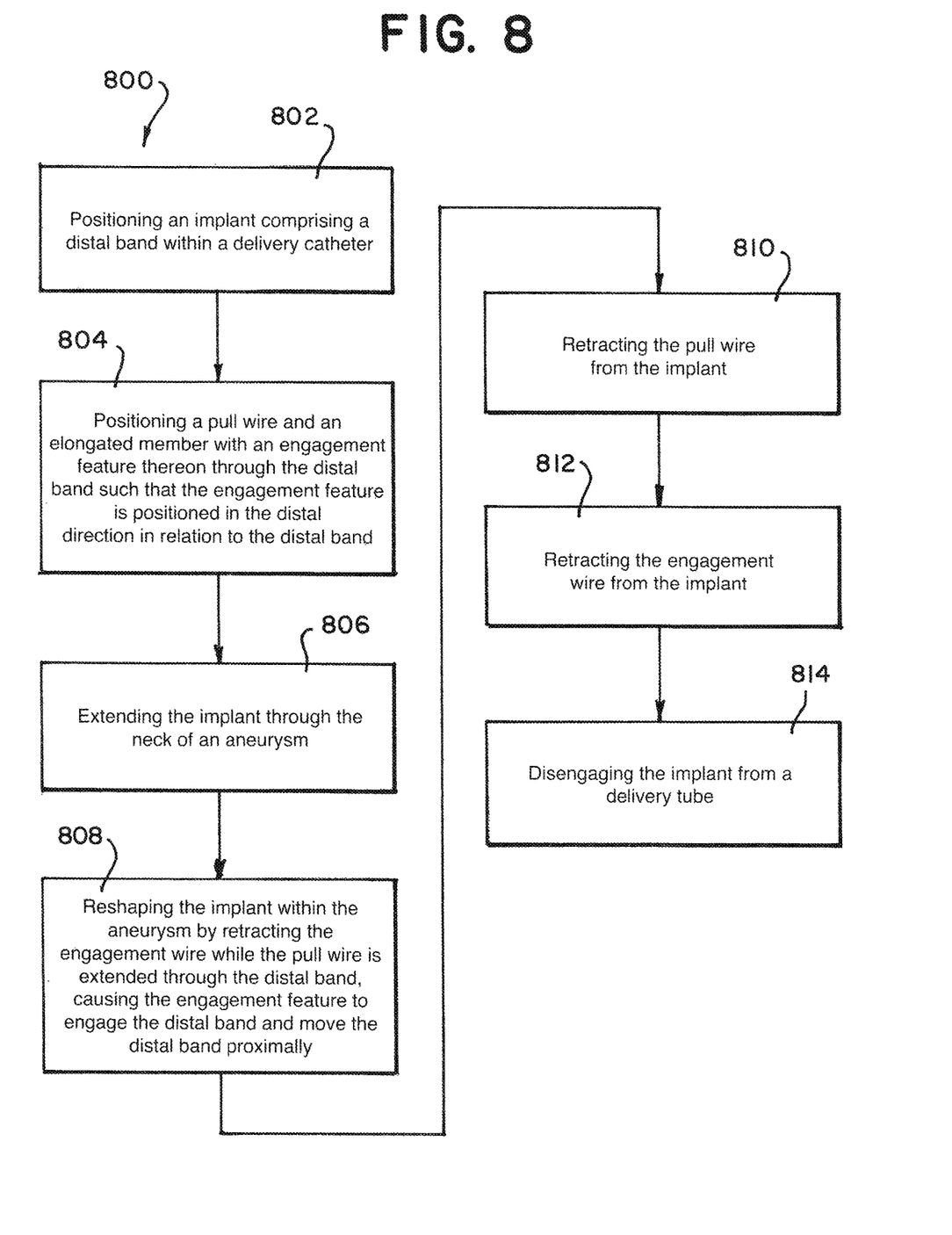
FIG. 8 is a flow diagram outlining example method steps that can be carried out during deployment of an exemplary implant according to aspects of the present invention.

FIG. 8 illustrates an example method 800 for constructing or configuring an implant and a delivery system such as an exemplary implant 100 and/or an exemplary delivery system 200 as presented herein, variations thereof, or alternatives thereof as would be appreciated and understood by a person of ordinary skill in the art.

At block 802, an implant having a distal band can be positioned within a guide catheter. The distal band and guide catheter can be a distal band 124 and guide catheter 310 as presented herein, a variation thereof, or an alternative thereof as would otherwise be appreciated and understood by a person of ordinary skill in the art. In some examples, a delivery tube can also be positioned within the guide catheter, proximal to the implant. The delivery tube can be a delivery tube 210 as presented herein, a variation thereof, or alternative thereof as would be appreciated and understood by a person of ordinary skill in the art. The delivery tube, guide catheter, and implant can be positioned as presented herein or as otherwise would be appreciated and understood by a person of ordinary skill in the art. Additionally, or alternatively, the delivery tube can be a hollow push rod 320 as presented herein, a variation thereof, or an alternative as would be appreciated and understood by a person of ordinary skill in the art. In such an example, the hollow push rod can be positioned within the guide catheter, proximal to the implant as presented herein or otherwise positioned as would be appreciated and understood by a person of ordinary skill in the art.

At block 804 a pull wire and an engagement wire are extended through the aperture of the loop wire and the lumen of the proximal ring. The pull wire, engagement wire, loop wire, and proximal ring can each respectively be a pull wire 220, engagement wire 230, loop wire 218, and proximal ring 122 as presented herein, a variation thereof, or an alternative thereof as would be appreciated and understood by a person of ordinary skill in the art. In some examples, the engagement wire 230 can be extended through the aperture 218a of the loop wire 218 before the pull wire 220 can be extended through the aperture 218a of the loop wire 218. Alternatively, the engagement wire 230 can be extended through the lumen 126 of the proximal ring 122 before the pull wire 220 can be extended through the lumen 126 of the proximal ring 122. In some examples, the engagement wire 230 need not be extended through the aperture 218a of the loop wire 218. In some examples, the pull wire 220 need not be extended though the aperture 218a of the loop wire 218. In some examples, neither the pull wire 220 nor the engagement wire 230 is extended through aperture 218a of the loop wire 218 and the detachment feature 123 need not be present. The pull wire 220 and the engagement wire 230 can be extended through the lumen 125 of the braid 110. In some examples, the engagement wire 230 can be extended though the lumen 125 of the braid 110 before the pull wire 220 can be extended through the lumen 125 of the braid 110. The pull wire 220 and the engagement wire 230 are extended through the lumen 128 of the distal band 124. In some examples, the engagement wire 230 can be extended though the lumen 128 of the distal band 124 before the pull wire 220 can be extended through the lumen 128 of the distal band 124. The implant 100 with the pull wire 220 and the engagement wire 230 therethrough can be positioned within a delivery catheter 310 such that the engagement feature 238 can be positioned in the distal direction in relation to the distal band 124.

At block 806, the implant 100 can pass though the neck 16 of the aneurysm 10, to enter the aneurysm's sac 12 by pushing the implant 100 using either a hollow push rod 320 or a delivery tube 210. In some examples, the distal end of the hollow push rod 320 can engage the proximal band 122 of the implant 100 permitting the hollow push rod 320 to push the implant 100 into the sac 12 of the aneurysm 10. In some examples, the detachment feature 123 can be secured to the notch 216 of the delivery tube 210 via the loop wire 218, allowing the delivery tube 210 to push the implant 100 into the sac 12 of the aneurysm 10.

At block 808, the implant 100 can be reshaped within the sac 12 by retracting the engagement wire 230 in a proximal direction while the pull wire 220 remains extended though the lumen 128 of the distal band 124. This causes the distal band 124 to move in a proximal direction, thereby reshaping the braid 110.

At block 810, the pull wire 220 can be retracted through the lumen 128 of the distal ring 124, the lumen 125 of the braid 110, and the lumen 126 of the proximal band 122 in a proximal direction. In some examples the pull wire 220 can be retracted through the aperture 218a of the loop wire 218.

At block 812, the engagement wire 230 can be retracted through the lumen 128 of the distal band 124, the lumen 125 of the braid 110, and the lumen 126 of the proximal band 122 in a proximal direction. In some examples the engagement wire 230 can be retracted through the aperture 218a of the loop wire 218.

At block 814, the implant 100 can be disengaged from the delivery system 200 via the retraction of the delivery tube 210, resulting in loop wire 218 to fall out of the opening 123a of the detachment feature 123, and thus allowing the detachment feature 123 to detach from the notch 216 of the delivery tube 210. Alternatively, the hollow push rod 320 pushes the implant 100 out of the guide catheter 310 and into the sac 12 without the use of the detachment feature 123 or the loop wire 218.

Figure 9:
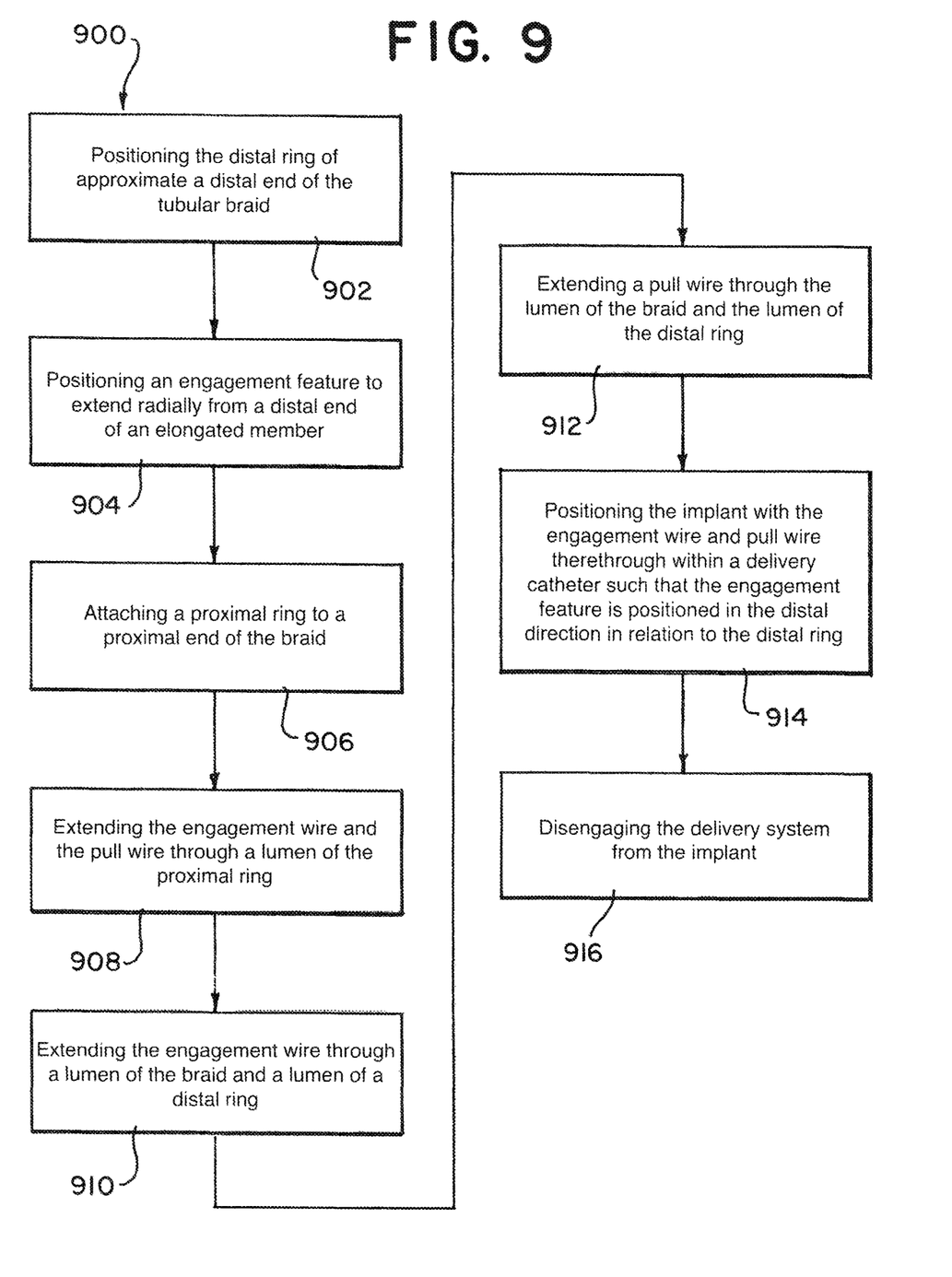
FIG. 9 is a flow diagram outlining example method steps for constructing an exemplary system according to aspects of the present invention.

FIG. 9 illustrates an example method 900 for deploying an implant using a delivery system such as an exemplary implant 100 and/or an exemplary delivery system 200 as presented herein, variations thereof, or alternatives thereof as would be appreciated and understood by a person of ordinary skill in the art.

At block 902, a distal ring can be positioned along a central axis approximate the distal end of a tubular braid. The distal ring and tubular braid can each respectively be a distal ring 124 and tubular braid 110 as presented herein, a variation thereof, or an alternative thereof as would be appreciated and understood by a person of ordinary skill in the art. The distal ring 124 can be attached to the distal end 114 of the tubular braid 110.

At block 904, the delivery system can include an engagement wire comprising an engagement feature and elongated member, and the engagement feature can be positioned at the distal end of the elongated member. The engagement wire can be an engagement wire 230 as presented herein, a variation thereof, or an alternative thereof as would be appreciated and understood by a person of ordinary skill in the art. The engagement feature 238 can extend radially from a distal end 234 of the elongated member 236. The engagement feature can be formed by grinding, welding, gluing, or other means as would be appreciated and understood by a person of ordinary skill in the art. For instance, polymer or metal sleeves can be affixed to a portion of the core wire, the core wire can form the elongated member of the engagement wire, and the sleeves can be ground down to the desired shape to form the engagement feature. Alternatively, the engagement feature can be formed by creating a weld bead on the end of a core wire, the core wire forming the elongated member of the engagement wire.

At block 906, a proximal ring can be positioned at the proximal end of the braid. The proximal ring can be a proximal ring 122 as presented herein, a variation thereof, or an alternative thereof as would be appreciated and understood by a person of ordinary skill in the art. The proximal ring 122 can be attached to the proximal end 112 of the tubular braid 110. In some examples, a detachment feature such as a detachment feature 123 presented herein, variation thereof, or alternative thereof can be attached to the proximal ring 122.

At block 908, a pull wire 220 and the engagement wire 230 are extended through the aperture 218a of a loop wire 218 and the lumen 126 of the proximal ring 122. The pull wire and loop wire can each respectively be a pull wire 220 and loop wire 218 as presented herein, a variation thereof, or an alternative thereof as would be appreciated and understood by a person of ordinary skill in the art. The loop wire 218 can be affixed to a delivery tube such as a delivery tube 210 presented herein, variation thereof, or alternative thereof as would be appreciated and understood by a person of ordinary skill in the art. Extension of the loop wire 218 and/or pull wire 220 through the aperture 218a of the loop wire 218 can serve to releasably secure the implant 100 to the delivery tube 210. In an exemplary system, the engagement wire 230 can be extended through the aperture 218a of the loop wire 218 before the pull wire 220 can be extended through the aperture 218a of the loop wire 218. In another exemplary system, the engagement wire 230 can be extended through the lumen 126 of the proximal ring 122 before the pull wire 220 can be extended through the lumen 126 of the proximal ring 122. In yet another exemplary system, the engagement wire 230 need not extend through the aperture 218a of the loop wire 218. In still another exemplary system, the pull wire 220 need not extend though the aperture 218a of the loop wire 218. In still yet another exemplary system, neither the pull wire 220 nor the engagement wire 230 extend through aperture 218a of the loop wire 218 and the detachment feature 123 need not be present.

At block 910, the pull wire 220 and the engagement wire 230 are extended through the lumen 125 of the tubular braid 110. In an exemplary system, the engagement wire 230 can be extended though the lumen 125 of the tubular braid 110 before the pull wire 220 can be extended through the lumen 125 of the tubular braid 110.

At block 912, the pull wire 220 and the engagement wire 230 are extended through the lumen 128 of the distal ring 124. In an exemplary system, the engagement wire 230 can be extended though the lumen 128 of the distal ring 124 before the pull wire 220 can be extended through the lumen 128 of the distal ring 124.

At block 914, the implant 100 with the pull wire 220 and the engagement wire 230 therethrough can be positioned within a delivery catheter 310 such that the engagement feature 238 is positioned in the distal direction in relation to the distal ring 124.

At block 916, the implant 100 can be disengaged from the delivery system 200 via the retraction of the pull wire 220 and the engagement wire 230 from the lumen 128 of the distal ring 124, the lumen 125 of the tubular braid 110, and the lumen 126 of the proximal ring 122. In an exemplary system, at least one of the pull wire 220 or the engagement wire 230 can be retracted from the aperture 218a of the loop wire 218.

The descriptions contained herein are examples of embodiments of the invention and are not intended in any way to limit the scope of the invention. As described herein, the invention contemplates many variations and modifications of the implant system, including alternative geometries of elements and components described herein, alternative braid shapes, utilizing one or more of several means for braiding, knitting, weaving, or otherwise forming the braid, utilizing alternative materials for each component or element (e.g. radiopaque materials, memory shape materials, polymers, metals, etc.), utilizing additional components to perform functions described herein or not described herein. These modifications would be apparent to those having ordinary skill in the art to which this invention relates and are intended to be within the scope of the claims which follow.

What is claimed is:

1. A system comprising:
an engagement wire comprising an elongated member and an engagement feature disposed at a distal end of the elongated member;
a pull wire; and
an implant comprising:
a delivery tube detachably attached to the implant;
a loop wire affixed to the delivery tube;
a braid movable from a delivery shape sized to traverse a catheter to an implanted shape sized to occlude an aneurysm neck;
a proximal ring and a distal ring affixed to the braid; and
a detachment feature attached to the proximal ring and comprising an opening therethrough, the loop wire extending through the opening;
wherein, when the braid is in the delivery shape, the pull wire and the elongated member extend through the distal ring and the engagement feature is in a distal direction in relation to the distal ring,
wherein the pull wire and the elongated member are movable in a proximal direction to engage the engagement feature to the distal ring and move the distal ring proximally, and
wherein the braid is movable from the delivery shape to the implanted shape upon a proximal movement of the distal ring.

2. The system of claim 1,
wherein, when the braid is in the delivery shape, the pull wire and the elongated member extend through the proximal ring, and
wherein, when the braid is in the delivery shape, the proximal ring is in the proximal direction in relation to the distal ring.

3. The system of claim 2, further comprising:
wherein the pull wire and the elongated member extend through the loop wire, and
wherein the pull wire is movable to exit the loop wire,
wherein the elongated member and the engagement feature are moveable to exit the loop wire after the pull wire has exited the loop wire, and
wherein the loop wire is movable to exit the opening when both of the pull wire and the elongated member exit the loop wire.

4. The system of claim 3,
wherein the delivery tube comprises a notch approximate a distal end of the delivery tube, and
wherein the detachment feature is positioned within the notch.

5. The system of claim 2, further comprising:
a hollow push rod, wherein, the hollow push rod engages the proximal ring of the implant; and
wherein the hollow push rod includes an inner diameter, the inner diameter being greater than a sum of a diameter of the pull wire and a diameter of the elongated member.

6. The system of claim 1, wherein a diameter of the engagement feature is less than an inner diameter of the distal ring.

7. The system of claim 1, wherein an inner diameter of the distal ring is greater than a sum of a diameter of the pull wire and a diameter of the elongated member; and
wherein the inner diameter of the distal ring is less than a sum of the diameter of the pull wire and a diameter of the engagement feature.

8. The system of claim 1, wherein the engagement feature is asymmetric about one or more axis.

* * * * *